US006639040B1

(12) United States Patent
Slack et al.

(10) Patent No.: US 6,639,040 B1
(45) Date of Patent: Oct. 28, 2003

(54) CONTINUOUS PROCESS FOR THE PRODUCTION OF MDI ALLOPHANATES

(75) Inventors: William E. Slack, Moundsville, WV (US); Hersel T. Kemp, II, New Martinsville, WV (US); William E. Miller, St. Clairsville, OH (US)

(73) Assignee: Bayer Corporation, Pittsburgh, PA (US)

( * ) Notice: Subject to any disclaimer, the term of this patent is extended or adjusted under 35 U.S.C. 154(b) by 0 days.

(21) Appl. No.: 10/170,915

(22) Filed: Jun. 13, 2002

(51) Int. Cl.[7] .................................................. C08G 18/16
(52) U.S. Cl. ........................ 528/49; 560/25; 560/27
(58) Field of Search .................... 560/25, 27; 528/49

(56) References Cited

U.S. PATENT DOCUMENTS

| 4,160,080 A | 7/1979 | Köenig et al. ................ 528/59 |
| 4,738,991 A | 4/1988 | Narayan ..................... 521/124 |
| 4,866,103 A | 9/1989 | Cassidy et al. ............. 521/159 |
| 5,319,053 A | 6/1994 | Slack et al. .................... 528/48 |

FOREIGN PATENT DOCUMENTS

GB          994890       6/1965

*Primary Examiner*—Rachel Gorr
(74) *Attorney, Agent, or Firm*—Joseph C. Gil; N. Denise Brown

(57) ABSTRACT

This invention relates to a continuous process for the production of allophanate modified diphenylmethane diisocyanates having an NCO group content of 19 to 32% and an urethane content of less than 2 area % by GPC analysis. The process comprises (1) continuously reacting (a) diphenylmethane diisocyanate and (b) an alcohol, in the presence of (c) at least 25 ppm of an allophante catalyst, based on the combined weight of the diphenylmethane diisocyanate and the alcohol, in a reactor in an oxygen-free environment; (2) continuously treating the product exiting the reactor with a catalyst stopper at the reaction temperature; and (3) cooling the resultant product.

24 Claims, No Drawings

CONTINUOUS PROCESS FOR THE PRODUCTION OF MDI ALLOPHANATES

BACKGROUND OF THE INVENTION

This invention relates to a continuous process for the production of allophanate-modified diphenylmethane diisocyanates having an NCO group content of 19 to 32% by weight and an urethane content of less than 2 area % as determined by GPC analysis. The process comprises (1) continuously reacting (a) diphenylmethane diisocyanate and (b) an alcohol, in the presence of (c) at least 25 ppm of an allophanate catalyst, based on the combined weight of the diphenylmethane diisocyanate and the alcohol, in a reactor in an oxygen-free environment; (2) continuously treating the product exiting the reactor with a catalyst stopper at the reaction temperature; and (3) cooling the resultant product. The allophanate catalyst can be dissolved in either the diphenylmethane diisocyanate or in the alcohol.

Allophanate-modified di- and poly-isocyanates are known and described in, for example, U.S. Pat. Nos. 4,160,080, 4,738,991, 4,866,103, 5,319,053 and GB 994,890.

U.S. Pat. No. 4,160,080 discloses a process for the preparation of allophanates which containing aliphatically and/or cycloaliphatically bound isocyanate groups in which compounds containing urethane groups are reacted with polyisocyanates having aliphatic and/or cycloaliphatic isocyanate groups, in the presence of a strong acid. The process is generally conducted at a temperature of from 90 to 140° C. for about 4 to about 20 hours. All of the working examples describe a batch process.

Storage-stable polyisocyanates having allophanate linkages are disclosed by U.S. Pat. No. 4,738,991. These polyisocyanates containing allophanate linkages are prepared by reacting an organic polyisocyanate with a mono- or polyhydric compound in the presence of an organo-metallic catalyst. The catalyst is then deactivated by a compound such as an inorganic acid, an organic acid, an organic chloroformate or an organic acid chloride. Only a batch process is described. All of the examples use toluene diisocyanate with ethylene glycol to form the polyisocyanates having allophanate linkages.

Polyisocyanate compositions are disclosed in U.S. Pat. No. 4,8661,103. These polyisocyanates comprise the reaction product of an alcohol or thiol having an average functionality of from about 1.5 to about 4 and an average equivalent weight of at least 500 with at least 2 equivalents per hydroxyl and/or thiol equivalent of an organic polyisocyanate (including the 4,4'- and 2,4'- isomers of diphenylmethane diisocyanate) under conditions such that at least about 20% of the initially formed urethane and/or thiourethane groups are converted to allophanate and/or thioallophanate groups. The only working example illustrating the preparation of an allophanate modified isocyanate uses a batch process.

U.S. Pat. No. 5,319,053 discloses stable, liquid, allophanate-modified diphenylmethane diisocyanates having NCO group contents of 12 to 32.5% by weight, and prepolymers of these stable, liquid, allophanate-modified diphenylmethane diisocyanates. Batch processes for the production of these products are also disclosed. The allophanate-modified diphenylmethane diisocyanates of this reference may be prepared by (1) pre-reacting the diphenylmethane diisocyanate with an aliphatic alcohol to form a urethane, which is subsequently converted to an allophanate; or (2) reacting the aliphatic alcohol, diphenylmethane diisocyanate and catalyst to form the allophanate directly. Although the batch process described therein has been used successfully in commercial operations, it is desirable to produce substantially identical products via a continuous process due to lower costs, resulting from smaller reactors having substantially higher throughput.

Allophanate modified polyisocyanates are also disclosed in GB 994,890. These are obtained by reacting an amount in excess of n moles of an organic diisocyanate with one mole of a urethane isocyanate of the specified formulation, with the reaction being carried out under conditions such that substantially one molecule of diisocyanate reacts with each urethane group present, as indicated by the measured isocyanate group content of the reaction mixture. Suitable conditions for the reaction include heat alone, or in the presence of a catalyst such as, for example, a metal carboxylate, a metal chelate or a tertiary amine. Only batch processes are described for the preparation of allophanate-modified isocyanates.

Advantages of the present invention include a novel method of preparing, at various NCO group contents, a consistent allophanate product at a lower cost from MDI and alcohols in the presence of an allophanate catalyst using inexpensive equipment. The present invention also describes the most probable method for introduction of the allophanate catalyst and the limitations of using MDI as a vehicle to deliver the allophanate catalyst.

SUMMARY OF THE INVENTION

This invention relates to a continuous process for the production of allophanate modified diphenylmethane diisocyanates having NCO group contents of from about 19 to about 32% by weight, and having a urethane content of less than 2 area % by GPC analysis. This process comprises:

(1) continuously reacting
  (a) diphenylmethane diisocyanate comprising
    (i) from about 0 to about 60% by weight of 2,4'-diphenylmethane diisocyanate,
    (ii) less than about 6% by weight of 2,2'-diphenylmethane diisocyanate, and
    (iii) the balance being 4,4'-diphenylmethane diisocyanate, with the sum of the %'s of (a)(i), (a)(ii) and (a)(iii) totaling 100% by weight of (a), the diphenylmethane diisocyanate; and
  (b) an alcohol; in the presence of
  (c) at least 25 ppm of an allophanate catalyst, based on the combined weight of the diphenylmethane diisocyanate and the alcohol;
in at least one reactor at a temperature of from 80 to 110° C., preferably 90 to 100° C., most preferably about 90° C., for about 0.5 to 4 hours, preferably 1 to 2 hours and most preferably about 1 to about 1.5 hours, in an oxygen free environment (preferably in the presence of an inert gas such as, for example, nitrogen;

(2) continuously treating the product exiting the reactor with a catalyst stopper, with the stopper being present in an amount such that there is at least 1 mole of stopper for each mole of catalyst and more preferably from 1 mole to 4 moles of stopper for each mole of catalyst, and the stopper being added at the reaction temperature; and (3) cooling the resultant product, preferably to a temperature of from about 25 to about 30° C.

DETAILED DESCRIPTION OF THE INVENTION

The continuous process of the present invention can be performed, for example, in at least one reactor, wherein the reactants are continuously fed into the reactor and the product continuously exits the reactor. It is preferred to use either a plug-flow reactor, or a cascade overflow reactor system. In cascade-overflow reactor system, it is preferred that the system comprise at least two (2) reactors, more preferably from two (2) to four (4) reactors, and most preferably three (3) reactors.

Suitable reaction temperatures for the first step, i.e. continuously reacting diphenylmethane diisocyanate with an alcohol, in the present process are from about 80 to about 110° C., preferably from about 90 to about 100° C. and most preferably about 90° C., for time periods of from about 0.5 to about 4 hours, preferably about 1 to about 2 hours, and most preferably about 1 to about 1.5 hours. These residence times represent the total reaction time for all reactors present.

Suitable reactor systems and feed systems for the present continuous process have oxygen-free environments. It is preferred that the entire system including feed systems as well as the reactors are purged with an inert gas. Some examples of inert gases suitable for this purpose include compounds such as nitrogen, helium, neon, argon, etc. Nitrogen is a particularly preferred inert gas for the present invention.

Suitable (a) diphenylmethane diisocyanates for the present process include those which comprise:

(i) from about 0 to about 60% by weight, preferably from about 1 to about 3% by weight, and most preferably from about 1 to about 2% by weight of the 2,4'-isomer of diphenylmethane diisocyanate;

(ii) less than about 6% by weight, preferably from about 0 to about 1% by weight, and most preferably from about 0 to about 0.2% by weight of the 2,2'-isomer of diphenylmethane diisocyanate; and (iii) the balance being 4,4'-diphenylmethane diisocyanate; with the sum of the %'s by weight of (a)(i), (a)(ii) and (a)(iii) totaling 100% by weight of (a) the diphenylmethane diisocyanate component.

It is preferred that diphenylmethane diisocyanates suitable for the present invention have an acidity of less than 10 ppm (as HCI), more preferably less than 5 ppm and most preferably less than 3 ppm.

Suitable alcohols for component (b) of the present invention include aliphatic alcohols and aromatic alcohols. Some examples of suitable aliphatic alcohols include those having from 1 to 36 carbon atoms, preferably from 4 to 16 carbon atoms, and most preferably 4 to 8 carbon atoms. Illustrative but non-limiting examples of these aliphatic alcohol's can be selected from the group consisting of cycloaliphatic alcohol's, aliphatic alcohols containing aromatic groups, aliphatic alcohols containing groups that do not react with isocyanates, e.g. ether groups and halogens such as, for example, chlorine and bromine. Other specific examples of some suitable aliphatic alcohols include compounds such as 2-butanol, cetylalcohol, cyclohexanol, 2-methoxyethanol, 2-bromoethanol, isobutyl alcohol, isooctyl alcohol, etc. A particularly preferred aliphatic alcohol is isobutyl alcohol.

Examples of suitable aromatic alcohols are those compounds containing 6 to 18 carbon atoms, preferably 6 to 12 carbon atoms, Wherein the hydroxyl group is directly attached to the aromatic ring. Some suitable aromatic alcohols include, for example, phenol, 1-naphthol, and substituted phenols such as cresol and substituted naphthols such as 3-methyl-1-naphthol. Preferred aromatic alcohols are phenol and the. substituted phenols.

The present invention also requires a suitable allophanate catalyst. Some examples of these catalysts include zinc acetylacetonate, zinc 2-ethylhexanoate, cobalt 2-ethylhexanoate, cobalt naphthenate, lead linoresinate, etc. Zinc acetylacetonate is a preferred catalyst.

In accordance with the present invention, the allophanate catalyst is present in a sufficient amount such that there is at least 25 ppm of catalyst, based on the combined weight of the diphenylmethane diisocyanate and the alcohol components. It is preferred that there are at least 40 ppm of catalyst, and most preferably from 40 to 75 ppm of catalyst present, based on the combined weight of the diphenylmethane diisocyanate and the alcohol components.

Once the product leaves the reactor (or the last reactor if a cascade-overflow reactor system is being used), the product should be maintained at the same temperature, or close to it, until after the addition of a catalyst stopper. This is because if the product is allowed to cool before the stopper is added, it leads to the promotion of polymeric allophanate species having a functionality greater than 2.0.

Suitable catalyst stoppers for the present invention include those which are generally known to be effective stoppers for batch processes to form allophanate-modified isocyanates. Some examples include acidic materials such as anhydrous hydrochloride acid, sulfuric acid, bis(2-ethylhexyl)hydrogen phosphate, benzoyl chloride, Lewis acids, etc. Benzoyl chloride is the preferred stopper. The amount of stopper to be added is generally such that there is at least 1 mole of stopper present for each mole of catalyst present, and more preferably from 1 mole to 4 moles of stopper for each mole of catalyst present.

Once the addition of-the catalyst stopper is complete, preferably a few minutes after addition of the stopper, the resultant product is cooled. It is preferred that the product is cooled to a temperature between 25 and 30° C.

In accordance with the present invention, the allophanate catalyst may be dissolved in the diphenylmethane diisocyanate component and introduced into the reactor as a mixture, with the alcohol component being added separately, or the allophanate catalyst may be dissolved in the alcohol component and introduced into the reactor as a mixture, with the diphenylmethane diisocyanate component being added separately. It is also possible that some allophanate catalyst be dissolved in each of the two components, i.e. the alcohol component and the diphenylmethane diisocyanate component. The amount of allophanate catalyst added to either or both components should be such that there is at least 25 ppm of allophanate catalyst present, based on the combined weight of the diphenylmethane diisocyanate component and the alcohol component.

When the allophanate catalyst is added to the diphenylmethane diisocyanate component, the mixture should be stored at temperatures of no more than 60° C., preferably from 40 to 50° C. and most preferably from 40 to 42° C. In addition, the mixture of diphenylmethane diisocyanate should be used within 20 hours of when it is prepared, and preferably within 8 hours of being prepared. It has been found that if this mixture of MDI-allophanate catalyst is used after 20 hours, the color of the resultant allophanate-modified diphenylmethane diisocyanates increased and was darker, with slightly higher viscosities due to the formation of side products (i.e. dimers and/or trimers).

In the present invention, it is preferred that the allophanate catalyst is added to the alcohol component. In this embodiment, the mixture should be stored at temperatures of no more than 50° C., preferably from 20 to 40° C. and most preferably from 20 to 30° C. In addition, the mixture of alcohol component and allophanate catalyst, when stored at temperatures between 45 and 50° C., should be used within 3 weeks of when it is prepared, and preferably within 2 weeks of being prepared. It has been found that if this mixture of alcohol-allophanate catalyst is used after 3 weeks, the catalyst loses some of its reactivity and could lead to urethane not being completely converted to allophanate (i.e. >2 area % by GPC). In addition, the mixture of alcohol component and allophanate catalyst, when stored at temperatures <40° C., should be used within 3 months of when it is prepared. This embodiment allows more flexibility in terms of length of time a mixture of alcohol-catalyst can be stored prior to being used in the presently claimed process and temperatures at which these mixtures can be stored and/or used at, without adversely affecting the allophanate-modified diphenylmethane diisocyanates produced by this continuous process.

The allophanate-modified diphenylmethane diisocyanates produced by the presently claimed continuous process have essentially identical NCO $_1$group contents as those allophanate-modified diphenylmethane diisocyanates prepared by a batch process and as described in, for example, U.S. Pat. No. 5,319,053, the disclosure of which is herein incorporated by reference. The continuous cascade process gives the expected small variation in the allophanate oligomer distribution, however, these products are interchangeable with the products of a batch process.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all parts and percentages are parts by weight and percentages by weight, respectively.

EXAMPLES

A. Standard Batch Process (Comparative)

The standard procedure for making the MDI allophanate by a batch process consisted of adding the 4,4'-MDI at 50° C. to a 3-neck flask equipped with a stirrer, thermometer, condenser, and a nitrogen blanket. The isobutanol was added to the MDI at 50° C. When the exotherm was completed, 75 ppm of zinc acetylacetonate was added. The reaction mixture was heated to 90° C. and held for 90 minutes. At the end of this time, 150 ppm of benzoyl chloride stopper was added, and the reaction mixture was cooled to 25° C.

B. Zinc Acetylacetonate Stability Study in MDI

In this procedure, 81 ppm zinc acetylacetonate was dissolved in the MDI, and then held either at 42° C. or 52° C. until used. A series of Batch runs were done using the procedure described above in Section A with the two materials over several weeks. The products were compared to the same product made using the standard procedure as described in Section A.

C. Zinc Acetylacetonate Stability Study in Isobutanol

In this procedure, 1042 ppm zinc acetylacetonate was dissolved in the isobutanol, and held at either 25° C., 42° C., or 52° C. until used. A series of batch runs were done using the procedure description above in Section A with the three materials over several weeks. The results were compared to the same product made using the standard procedure as described in Section A.

D. Cascade Process

The set-up used for the demonstration of a continuous cascade process for the preparation of the isobutanol 4,4'-MDI allophanate consisted of 3 overflow reactors equipped with thermocouples and heating mantles. The first reactor had an overflow capacity of 5000 grams and had a nitrogen purge which extended through all three reactors. The second and third reactors had an overflow capacity of 833 grams each. Using this arrangement of equipment, the zinc acetylacetonate was dissolved in either the isobutanol or in the MDI, and the reactants (i.e. either isobutanol containing ZnAcAc, and MDI; or MDI containing ZnAcAc, and isobutanol) were pumped into the first reactor using Zenith pumps at a ratio which would give the desired % NCO allophanate. The MDI and isobutanol were both delivered into the reactor just above the stirrer. The alcohol feed was held at about 25° C. and the MDI feed at about 50° C. All three reactors were held at 90° C. The 90° C. overflow from the third reactor was treated with benzoyl chloride stopper and then cooled to 25–30° C. in the final product receiver.

The residence time for all runs reported here was 80 minutes (60-10-10) which is equal to pumping of 83.3 g per minute (MDI +isobutanol).

The concentration of the zinc acetylacetonate dissolved in either the MDI or the isobutanol feeds are listed below in Table A for the three different allophanate products prepared by this process.

TABLE A

| % NCO Allophanate | Isobutanol, ppm ZnAcAc | MDI, ppm ZnAcAc |
|---|---|---|
| 23.0 | 1042 | 0 |
| 23.0 | 0 | 81 |
| 26.0 | 1442 | 0 |
| 26.0 | 0 | 79 |
| 29.0 | 2420 | 0 |
| 29.0 | 0 | 77 |

Cascade Results:

Table 1 lists the results for the different percent NCO allophanate products prepared by both the batch and cascade processes in which a 75 ppm zinc acetylacetonate catalyst level was used. This catalyst level was based on the total weight of the MDI and isobutanol. All the examples listed in Table 1 had a Gardner color of 1.

It appears that in the cascade process, the zinc acetylacetonate can bye dissolved in either the MDI or the isobutanol without having any significant affect on the final product's NCO content, viscosity, or urethane content.

TABLE 1

Batch and Cascade Process Results with 75 ppm Zinc Acetylacetonate

| Run # | Process | ZnAcAc Dissolved In | Area % Urethane by GPC | % NCO | Visc. @ 25° C., cps |
|---|---|---|---|---|---|
| 1. | C[1] | MDI | 0.46 | 28.9 | 42 |
| 2. | C[1] | Isobutanol | 0.32 | 28.8 | 44 |
| 3. | B[2] | Mixture | 0.11 | 28.9 | 38 |
| 4. | C[1] | MDI | 0.43 | 25.9 | 122 |
| 5. | C[1] | Isobutanol | 0.58 | 25.8 | 119 |
| 6. | B[2] | Mixture | 0.20 | 25.9 | 102 |
| 7. | C[1] | MDI | 0.89 | 22.9 | 506 |
| 8. | C[1] | Isobutanol | 0.90 | 23.1 | 510 |
| 9. | B[2] | Mixture | 0.76 | 22.9 | 460 |

[1]Continuous process
[2]Batch process make the 23.0% NCO a6lophanate. The results are given in Tables 2 and 3. Also, included in these tables, are the results for a standard 23% NCO allophanate using the batch procedure described in section A.

Table 2 shows that when the MDI-catalyst mixture stored at 42° C. was used to make the 23% NCO allophanate, the urethane content of the final product was low and the NCO content was correct, indicating that the catalyst was still active as an allophanate catalyst. However, the color of the final product increased from a Gardner 1 to a Gardner 3 when the MDI-catalyst mixture was stored for 20 hours before use. When the current batch process (as described in Section A above) was used for the production of the 23% allophanate, the allophanates had a Gardner color of 1. A trend to a higher viscosity final product was observed with longer storage at 42° C. of the MDI-catalyst mixture before use. This appears to be real since the $1^{st}$ allophanate oligomer in the GPC shows a trend down in area percent while the $2^{nd}$ allophanate oligomer shows an increase. A peak in the GPC that eluted between the $1^{st}$ and $2^{nd}$ allophanate oligomers, which was not resolved from the $2^{nd}$ allophanate oligomer appeared to be trimer. This accounted for the increase in the area percent of the $2^{nd}$ allophanate oligomer.

TABLE 2

Stability Study of Zinc Acetylacetonate-MDI Mixture at 42° C. as Determined by Preparation of the 23% NCO Allophanate in a Batch Reaction

| Run # | Days MDI Catalyst Solution held at 42° C. | % NCO | Visc. @ 25° C., cps | Gardner Color | Area Percent by GPC | | | |
|---|---|---|---|---|---|---|---|---|
| | | | | | Urethane | $1^{st}$ | $2^{nd}$* | $3^{rd}$ | $4^{th}$+ |
| 10. | 0 | 23.1 | 406 | 1 | 0.9 | 30.3 | 13.4 | 4.7 | 2.1 |
| 11. | 1 | 23.1 | 468 | 3 | 0.7 | 30.0 | 14.0 | 4.9 | 2.3 |
| 12. | 2 | 23.1 | 509 | 3 | 0.8 | 29.9 | 14.3 | 5.2 | 2.4 |
| 13. | 5 | 22.9 | 573 | 3 | 0.9 | 29.3 | 14.7 | 5.0 | 2.6 |
| 14. | 9 | 23.1 | 590 | 4 | 1.0 | 27.9 | 15.0 | 4.3 | 3.0 |
| 15. | 12 | 23.0 | 642 | 4 | 1.0 | 27.2 | 15.4 | 4.6 | 3.0 |
| Standard | — | 22.9 | 421 | 1 | 0.5 | 30.4 | 13.5 | 4.4 | 2.1 |

*Includes trimer

Results of Zinc Acetylacetonate Stability Study in MDI

The preferred allophanate catalyst for the present invention is zinc acetylacetonate, which is a solid. In order for a continuous process to conveniently use a solid catalyst, it must be dissolved in one of the liquid components. In the case of the MDI allophanate, this means the catalyst must be dissolved in either the MDI or in the isobutanol.

For the MDI approach to be viable, the zinc acetylacetonate MDI mixture must be solids free above 40° C. for several days and the catalyst must remain active as an allophanate catalyst without generating any side products such as dimer or trimer. In order to assess the viability of this method, 81 ppm zinc acetylacetonate was dissolved in MDI and a sample was held at both 42° C. and 52° C. In both cases, the MDI catalyst mixture turned yellow after about 2 hours storage at these temperatures. Over a period of time, batch runs were made using process A, the standard batch process, (90° C. for 90 minutes) using these materials to These trends are clearer in Table 3 which illustrates the stability of the MID-catalyst mixture stored at 52° C. In addition to the trend to higher molecular weight components and the obvious increase in viscosity of the final allophanate product, an increase in the urethane content of the allophanate product with storage at 52° C. of the MDI-catalyst mixture indicates the zinc acetylacetonate (i.e. the catalyst) is slowly losing its activity as an allophanate catalyst. The color of the final allophanate-modified product also continues to increase from Gardner 1 to Gardner 6 when the MDI-catalyst mixture is used after 16 days storage at 52° C.

A review of the results in Tables 2 and 3 indicates that dissolving the catalyst (zinc acetylacetonate) in MDI at temperatures between 40 and 50° C. is only suitable for a continuous process if the MDI-catalyst mixture is used within 8 hours of its mixing. This is due to changes in the color and the viscosity of the final product caused by the formation of side-products (i.e. dimers, trimers, etc.), and loss of catalytic activity of the zinc acetylacetonate.

TABLE 3

Stability Study of Zinc Acetylacetonate-MDI Mixture at 52° C. as Determined by Preparation of the 23% NCO Allophanate in a Batch Reaction

| Run # | Days MDI Catalyst Solution held at 52° C. | % NCO | Visc. @ 25° C., cps | Gardner Color | Urethane | 1st | 2nd* | 3rd |
|---|---|---|---|---|---|---|---|---|
| standard | — | 22.9 | 421 | 1 | 0.5 | 30.4 | 13.5 | 6.5 |
| 16. | 0 | 23.2 | 425 | 1 | 1.0 | 30.0 | 11.8 | 7.9 |
| 17. | 1 | 23.1 | 476 | 3 | 1.1 | 29.5 | 12.6 | 7.1 |
| 18. | 4 | 22.9 | 532 | 3 | 1.1 | 28.9 | 12.8 | 8.8 |
| 19. | 7 | 22.9 | 545 | 4 | 1.6 | 27.6 | 12.9 | 9.1 |
| 20. | 10 | 22.8 | 630 | 5 | 2.9 | 26.2 | 13.2 | |
| 21. | 14 | 22.8 | 685 | 5 | 1.4 | 27.1 | 13.2 | 11.1 |
| 22. | 15 | 22.8 | 746 | 5 | 2.6 | 25.6 | 13.7 | 11.7 |
| 23. | 16 | 22.7 | 845 | 6 | 1.4 | 26.5 | 13.2 | 12.3 |
| 24. | 21 | 22.8 | 950 | 6 | 3.3 | 23.4 | 13.6 | 14.5 |
| 25. | 24 | 22.7 | 1100 | 6 | 4.1 | 20.5 | 13.9 | 16.5 |

*Includes trimer

Results of Zinc Acetylacetonate Stability Study in Isobutanol

A second method for the use of zinc acetylacetonate as a catalyst in a continuous MDI allophanate process is to dissolve the zinc acetylacetonate in the isobutanol. For this method to be viable, the catalyst alcohol mixture must be solids free when stored at temperatures between 20 and 50° C. for an extended period of time, and the zinc acetylacetonate must retain its reactivity as an allophanate catalyst.

The practicality of this method was investigated by dissolving 1042 ppm zinc acetylacetonate in isobutanol and storing at 22, 42, and 52° C. These mixtures were then reacted with 4,4'-MDI using the standard allophanate reaction conditions (90° C. for 90 minutes) to make the 23% NCO allophanate (as described above in Section A). This required 7.2% by weight of the isobutanol-catalyst mixtures, which gives the standard 75 ppm catalyst level used for the MDI allophanate process.

Tables 4, 5, and 6 set forth the results for the preparation of the 23% NCO allophanate using these isobutanol-catalyst mixtures held at 22, 42, and 52° C., respectively. All the products listed in Tables 4, 5, and 6 have good color (i.e. a Gardner 1).

For the isobutanol-zinc acetylacetonate mixture stored at 22° C., a good consistent product resulted (see Table 4) over the 106 days it was tested. There was no sign in the GPC scans of the peak attributed to trimer. For the isobutanol-zinc acetylacetonate mixture stored at 42° C., similar results were found (see Table 5) over the 106 days it was tested. However, for the isobutanol-zinc acetylacetonate mixture held at 52° C., deterioration in the allophanate catalyst activity was observed, as illustrated by the high urethane in GPC scan of the final product, after 26 days of storage. Also, after 26 days, a peak in the GPC scan of the final product attributed to trimer appeared (see Table 6).

Based on these results, dissolving the zinc acetylacetonate catalyst in isobutanol and maintaining the temperature of this mixture at temperatures between 20 and 30° C. for use in a continuous process would be recommended.

In each example, the alcohol/Zn acetylacetonate solution was held at different temperatures and then used after the given days of storage to prepare the 23% NCO group content allophanate. In all tables, the information provided is data on the final allophanate-modified products.

TABLE 4

Stability Study of Zinc Acetylacetonate-Isobutanol Mixture at 22° C. as Determined by Preparation of the 23% NCO Allophanate in a Batch Reaction

| Run # | Days Mixture Held at 22° C. | % NCO | Visc. @ 25° C., cps | Urethane | 1st | 2nd | 3rd | 4th+ |
|---|---|---|---|---|---|---|---|---|
| 26. | 0 | 23.1 | 430 | 1.4 | 30.3 | 11.8 | 3.9 | 1.7 |
| 27. | 17 | 23.0 | 356 | 1.2 | 30.3 | 11.7 | 3.9 | 1.7 |
| 28. | 22 | 22.9 | 390 | 1.0 | 30.1 | 11.4 | 4.8 | 2.1 |
| 29. | 26 | 23.1 | 354 | 0.7 | 29.9 | 10.9 | 3.9 | 1.1 |
| 30. | 29 | 23.0 | 389 | 0.8 | 29.1 | 11.2 | 3.9 | 1.4 |
| 31. | 33 | 22.9 | 410 | 1.0 | 30.9 | 12.2 | 4.0 | 1.5 |
| 32. | 38 | 22.9 | 430 | 0.5 | 30.0 | 12.1 | 4.9 | 1.9 |
| 33. | 59 | 22.9 | 440 | 1.2 | 31.1 | 12.1 | 4.4 | 1.3 |
| 34. | 106 | 23.0 | 390 | 1.1 | 30.2 | 12.4 | 4.2 | 1.4 |

TABLE 5

Stability Study of Zinc Acetylacetonate-Isobutanol Mixture at 42° C. as Determined by Preparation of the 23% NCO Allophanate in a Batch Reaction

| Run # | Days Mixture Held at 42° C. | % NCO | Visc. @ 25° C., cps | Urethane | Area Percent by GPC 1st | 2nd | 3rd | 4th+ |
|---|---|---|---|---|---|---|---|---|
| 35. | 0 | 23.0 | 430 | 1.4 | 30.3 | 11.8 | 3.9 | 1.7 |
| 36. | 17 | 23.0 | 368 | 1.1 | 29.7 | 11.5 | 4.7 | 2.1 |
| 37. | 24 | 23.0 | 374 | 1.2 | 30.2 | 11.7 | 3.9 | 1.7 |
| 38. | 33 | 23.0 | 415 | 0.5 | 30.4 | 11.6 | 4.7 | 1.3 |
| 39. | 38 | 23.1 | 385 | 1.1 | 30.4 | 11.1 | 4.0 | 1.1 |
| 40. | 43 | 22.9 | 440 | 0.8 | 30.1 | 12.4 | 5.5 | 2.4 |
| 41. | 59 | 23.0 | 400 | 0.9 | 30.6 | 11.9 | 3.8 | 1.0 |
| 42. | 79 | 23.0 | 386 | 0.9 | 30.1 | 12.2 | 4.6 | 1.7 |
| 43. | 106 | 23.0 | 380 | 1.5 | 30.1 | 11.4 | 4.9 | 2.2 |

TABLE 6

Stability Study of Zinc Acetylacetonate-Isobutanol Mixture at 52° C. as Determined by Preparation of the 23% NCO Allophanate in a Batch Reaction

| Run # | Days Mixture Held at 52° C. | % NCO | Visc. @ 25° C., cps | Urethane | Area Percent by GPC 1st | 2nd | 3rd | 4th+ |
|---|---|---|---|---|---|---|---|---|
| 44. | 0 | 23.0 | 430 | 1.4 | 30.3 | 11.8 | 3.9 | 1.7 |
| 45. | 11 | 23.1 | 352 | 1.0 | 29.8 | 11.0 | 3.6 | 1.3 |
| 46. | 17 | 23.0 | 352 | 1.5 | 29.8 | 11.6 | 3.9 | 1.8 |
| 47. | 19 | 23.2 | 315 | 1.5 | 29.9 | 11.4 | 3.8 | 1.6 |
| 48. | 22 | 23.3 | 308 | 1.4 | 29.6 | 11.4 | 3.9 | 1.8 |
| 49. | 24 | 23.1 | 328 | 1.3 | 30.1 | 11.2 | 3.8 | 1.7 |
| 50. | 26* | 23.2 | 306 | 3.1 | 28.0 | 9.7 | 4.2 | 0.9 |
| 51. | 38* | 24.5 | 150 | 12.8 | 17.7 | 3.6 | 0.3 | — |
| 52. | 43* | 24.8 | 142 | 10.8 | 19.7 | 5.1 | 0.6 | — |

*The GPC scans of the products from the 26, 38, and 43 day runs had a trimer peak of 1.8, 3.5, and 3.6 area percent, respectively.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A continuous process for the production of an allophanate modified polyisocyanate having an NCO group content of 19 to 32%, and having an urethane content of less than 2 area % by GPC analysis, comprising (1) continuously reacting
      (a) diphenylmethane diisocyanate comprising:
         (i) from about 0 to about 60% by weight of 2,4'-diphenylmethane diisocyanate,
         (ii) less than 6% by weight of 2,2'-diphenylmethane diisocyanate, and
         (iii) the balance being 4,4'-diphenylmethane diisocyanate,
   with the sum of the %'s by weight of (1)(a)(i), (1)(a)(ii) and (1)(a)(iii) totaling 100% by weight of (1)(a) the diphenylmethane diisocyanate; and
      (b) an alcohol;
   in the presence of
      (c) at least 25 ppm of an allophanate catalyst, based on the combined weight of the diphenylmethane diisocyanate and the alcohol;
   in at least one reactor at a temperature of from 80 to 110° C. for 0.5 to 4 hours, in an oxygen-free environment;

(2) continuously treating the product exiting the reactor with a catalyst stopper at the reaction temperature; and
   (3) cooling the resultant product.

2. The process of claim 1, wherein (c) said allophanate catalyst is dissolved in (b) said alcohol component prior to being fed to the reactor.

3. The process of claim 2, wherein said alcohol component containing said catalyst is maintained at a temperature of from about 20 to about 40° C. in an oxygen-free environment.

4. The process of claim 1, wherein (c) said allophanate catalyst is dissolved in (a) said diphenylmethane diisocyanate component prior to being fed to the reactor.

5. The process of claim 4, wherein the diphenylmethane diisocyanate component containing said catalyst is used within 8 hours.

6. The process of claim 4, wherein said diphenylmethane diisocyanate component containing said catalyst is maintained at a sufficiently high temperature to liquefy the diphenylmethane diisocyanate but no more than about 60° C., in an oxygen-free environment.

7. The process of claim 6, wherein the temperature ranges from about 40° C. to about 50° C.

8. The process of claim 1, wherein the reactor comprises a plug-flow reactor.

9. The process of claim 1, wherein the reactor comprises a cascade overflow reactor system.

10. The process of claim 9, wherein the cascade overflow reactor systems comprises at least 2 reactors.

11. The process of claim 9, wherein the cascade overflow reactor systems comprises from 2 to 4 reactors.

12. The process of claim 9, wherein the cascade overflow reactor systems comprises 3 reactors.

13. The process of claim 1, wherein (1)(c) said allophanate catalyst preferably comprises zinc acetylacetonate.

14. The process of claim 1, wherein (1)(b) said alcohol is selected from the group consisting of aliphatic alcohols containing from 1 to 36 carbon atoms and aromatic alcohols containing from 6 to 18 carbon atoms.

15. The process of claim 14, wherein said aliphatic alcohols containing from 1 to 36 carbon atoms comprise isobutyl alcohol and said aromatic alcohols containing from 6 to 18 carbon atoms comprise phenol or a substituted phenol.

16. The process of claim 1, wherein (1) the continuous reaction of (a) the diphenylmethane diisocyanate, and (b) the alcohol, in the presence of (c) the allophanate catalyst, in at least one reactor is at a temperature ranging from 90 to 100° C. for 1 to 2 hours, in the presence of an inert gas.

17. The process of claim 16, wherein (1) the continuous reaction occurs at a temperature of about 90° C. for about 1 to about 1.5 hours.

18. The process of claim 1, wherein an inert gas provides the oxygen-free environment.

19. The process of claim 18, wherein the inert gas comprises nitrogen.

20. The process of claim 1, wherein the catalyst stopper is present in an amount such that there is at least 1 mole of stopper for each mole of catalyst.

21. The process of claim 1, wherein the catalyst stopper comprises benzoyl chloride.

22. The process of claim 1, wherein the catalyst stopper is present in an amount such that there are from 1 mole to 4 moles of stopper for each mole of catalyst.

23. The process of claim 1, wherein the resultant product in (3) is cooled to a temperature of from about 25 to about 30° C.

24. The process of claim 1, wherein (1)(a) said diphenylmethane diisocyanate comprises:
 (i) from about 1 to about 3% by weight of 2,4'-diphenylmethane diisocyanate,
 (ii) from about 0 to about 1% by weight of 2,2'-diphenylmethane diisocyanate, and
 (iii) the balance being 4,4'-diphenylmethane diisocyanate, with the sum of the %'s by weight of (1)(a)(i), (1)(a)(ii) and (1)(a)(iii) totaling 100% by weight of (1)(a) the diphenylmethane diisocyanate.

* * * * *